| United States Patent [19] | [11] | 4,225,583 |
|---|---|---|
| Switzer et al. | [45] | Sep. 30, 1980 |

[54] **INTRA-RESPIRATORY VACCINE FOR PREVENTION OF *BORDETELLA BRONCHISEPTICA* INFECTION AND METHOD OF USE**

[75] Inventors: William P. Switzer, Ames, Iowa; Daniel O. Farrington, Terre Haute, Ind.

[73] Assignee: Iowa State University Research Foundation, Inc., Ames, Iowa

[21] Appl. No.: 967,477

[22] Filed: Dec. 7, 1978

[51] Int. Cl.$^3$ .............................................. A61K 39/02
[52] U.S. Cl. ......................................................... 424/92
[58] Field of Search ............................................ 424/92

[56] References Cited

U.S. PATENT DOCUMENTS

| 3,127,318 | 3/1964 | Eversole et al. | 424/92 |
|---|---|---|---|
| 3,462,526 | 8/1969 | Ratuld et al. | 424/90 |
| 3,594,471 | 7/1971 | Hertzberger et al. | 424/89 |
| 3,608,066 | 9/1971 | Illartein | 424/46 |
| 3,755,557 | 8/1973 | Jacobs | 424/46 |
| 3,873,691 | 3/1975 | Kasuga et al. | 424/92 |
| 3,950,512 | 4/1976 | Emery et al. | 424/89 |
| 4,016,253 | 4/1977 | Switzer et al. | 424/92 |

FOREIGN PATENT DOCUMENTS

| 2892M | 11/1964 | France | 424/92 |
|---|---|---|---|
| 2307542 | 12/1976 | France | 424/92 |
| 1243601 | 8/1971 | United Kingdom | 424/92 |

OTHER PUBLICATIONS

Shimizu Infect. Immun., 22(2):318–321, Nov. 1978, "Prophylaxis of Bordetella Bronchiseptica Infection in Guinea Pigs by Intranasal Vaccination with Live Strain, TS–S34."

*Primary Examiner*—Shep K. Rose
*Attorney, Agent, or Firm*—Tilton, Fallon, Lungmus & Chestnut

[57] ABSTRACT

A vaccine for animals subject to *Bordetella bronchiseptica* infection comprises an aqueous suspension of viable cells of the modified *Bordetella bronchiseptica* previously identified as strain 55 and now further identified as ATCC strain No. 31437. Strain 55 is not merely attenuated and avirulent but has been modified so that it will colonize the respiratory mucosa of animals for only a limited time before it is cleared, causing no adverse effect on the animals. During the limited period of growth on the respiratory mucosa, however, strain 55 is capable of inducing local resistance to *B. bronchiseptica* infection. Swine are thereby protected against atrophic rhinitis and turbinate atrophy and dogs against tracheobronchitis (kennel cough).

12 Claims, No Drawings

INTRA-RESPIRATORY VACCINE FOR PREVENTION OF BORDETELLA BRONCHISEPTICA INFECTION AND METHOD OF USE

BACKGROUND AND PRIOR ART

Bordetella bronchiseptica is capable of infecting the nasal passages and respiratory tracts of many animals, particularly mammals. B. bronchispectica is the cause of atrophic rhinitis and pneumonia in swine. Harris and Switzer, Am. J. Vet. Res., 30, 1161-1166 (1969). A major lesion of the disease in swine is commonly referred to as "turbinate atrophy" because following the primary B. bronchiseptica infection, the nasal turbinate bones frequently undergo serious deterioration. See Switzer and Farrington U.S. Pat. No. 4,016,253 (1977).

In dogs, B. bronchiseptica has been characterized as the primary etiological agent in infectious canine tracheobronchitis more commonly known as kennel cough. Wright et al, Vet. Rec., Nov. 3, 1973, 486-487; Appel et al, Cornell Research Laboratory for Disease of Dogs, Laboratory Report, Series 2, No. 6 (May, 1976). The latter publication states that kennel cough is a highly contagious respiratory disease of dogs which, although not life-threatening, should be prevented. The disease causes suffering to the dogs and is unpleasant for dog owners. It is commonly transmitted when dogs are placed in kennels for boarding.

Other mammalian species are also afflicted with B. bronchiseptica infections of the respiratory tract. These include laboratory animals such as guinea pigs, rabbits, and rats, as well as animals raised for meat or fur, such as rabbits and chinchilla. See Nakagawa et al, Jap. J. Vet. Sci., 33(2), 53-60 (1971); Oldenburg et al, Monatshefte fur Veterinarmedizin, 27(19), 738-743 (1972); Burek et al, Lab. An. Sci., 22(66), 844-849 (1972); Ioakimidis et al, Kteniatrika Nea Thessaloniki, 2, 31-33 (1970). As with swine and dogs, the virulent B. bronchiseptica colonize the respiratory mucosa and thereby produce the clinical symptoms of the infection. B. bronchiseptica may also cause pneumonia in monkeys and other zoo animals. Graves, Lab. An. Car., 20(2), 246-250 (1970). Cats are carries of B. bronchiseptica and may spread the disease to other animals. Fisk et al, Lab. An. Sci., 23(1), 33-35 (1973).

Because of the economic loss to swine raisers due to turbinate atrophy, which is very prevalent in the United States and other countries, there has been a major research effort to develop an effective vaccine to protect swine against B. bronchiseptica.

Switzer and Harris found that the introduction of live cells of a low-virulence strain of B. bronchiseptica into the nasal cavities of non-immune swine would cause a relatively mild infection, and that thereafter the swine would be immune to further infection, and would thereby be protected against turbinate atrophy. See J. Vet. Res., 30, 1161-1166 (July, 1969). The attenuated strain of B. bronchiseptica tested by Switzer and Harris was designated strain D-1. Although introduction of strain D-1 into the nasal passages of swine protected the swine against turbinate atrophy, it was found that strain D-1 persisted in the nasal passages and produced a mild damage to the nasal epithelium. There was no evidence of reversion to a swine virulent form of B. bronchiseptica, but is was feared that strain D-1 could infect other animals such as dogs. The need for an effective live intranasal vaccine which has no adverse effect and which does not persist on the nasal mucosa has not been met until the present invention.

Parenteral vaccines for intramuscular injection were also the subject of extensive research. One of the first such experimental vaccines was prepared from a virulent strain of B. bronchiseptica (identified as strain B), but this whole-cell vaccine failed to induce adequate resistance to nasal infection as reported by Harris and Switzer, Am. J. Vet. Res., 30, 1161-1166 (July, 1969). The cells were killed to form the bacterin.

Kasuga et al U.S. Pat. No. 3,873,691 describes a parenteral vaccine which is prepared from virulent strains of B. bronchiseptica. In order to maintain the baceteria in virulent form (referred to as Phase I form in the patent), the patent teaches that the cultures should be grown in a medium containing blood, or in a special medium containing activated carbon or an ion exchange resin. It is believed that a parenteral vaccine prepared by the method of the Kasuga et al patent has been marketed for commercial use in Japan.

In the United States, the first successful swine vaccine for preventing turbinate atrophy is manufactured and sold by the Burns-Biotec Laboratories Division of Chrommalloy Pharmaceutical, Inc. in accordance with Switzer and Farrington U.S. Pat. No. 4,016,253. This patent describes a parenteral vaccine for intramuscular injection prepared from killed whole-cells of strain D-1 (ATCC No. 31124).

The resistance to B. bronchiseptica infection induced by parenteral vaccines such as the strain D-1 vaccine is different than the immunity produced by intranasal infection of swine with live B. bronchiseptica. Parenteral vaccination does not prevent nasal infection by virulent B. bronchiseptica, although it does accelerate nasal clearance of the infection, and effectively protects against the development of the gross lesions associated with atrophtic rhinitis, and the second destruction of the turbinate bones referred to as turbinate atrophy. Further, even a mild infection of the nasal passages of parenterally vaccinated swine may make the swine more susceptible to secondary infections of the respiratory tract.

The strain D-1 parenteral vaccine used commercially for swine has not been found to be effective for immunizing dogs against B. bronchiseptica. There is an increase in the circulating antibody titer, but the dogs still contract the infection and manifest symptoms of kennel cough. Further, the parenteral injection of strain D-1 vaccines may have undesirable side effects, including swelling at the site of the injection, anophylactic shock, and other toxic effects on the dogs. Some investigators (McCanldish-1976 and Shelton-1977) have reported experimental immunization of dogs against B. bronchiseptica infection with a parenteral vaccine. McCanldish et al., Vet. Rec., 98, 156-157 (1976); Shelton et al, Vet. Med./Small Animal Clinician, February, 1977, 189-193. However, another investigator (Appel-1977) has been unsuccessful in repeating the McCanldish or Shelton work. See Bemis, Greisen, and Appel, J. Infec. Disease, 135, 753-758 (May, 1977).

DESCRIPTION OF THE INVENTION

The vaccines of the present invention are prepared from live cells of a modified Bordetella bronchiseptica heretofore identified as strain 55. Prior to the filing of the present application, the term "strain 55" was a private code designation used by the inventors of this application, Willian P. Switzer and Daniel O. Farrington. No cultures of strain 55 were publicly available. In connection with the filing of this application, there has been placed on deposit with the American Type Cultures Collection, Rockville, Md., viable samples of strain 55 *B. bronchiseptica,* which can be used as seed cultures for producing the vaccine of the present invention. The deposited cultures of strain 55 are now further identified as ATCC strain No. 31437, which number will therefore also be used herein as an alternative designation to strain 55.

In 1973 Daniel O. Farrington and William P. Switzer published positive results of experiments using strain 55 intranasal vaccines for swine.

Proceedings the George A. Young Conference on Advances in Swine Repopulation and the *13th Annual Nebraska SPF Conference,* Lincoln, Nebraska, July 23–24, 1973, pp. 44–52. These and related experiments were more completely reported in the Ph.D. thesis of Daniel O. Farrington, entitled "Evaluation of Nasal Culturing Procedures and Immunization as Applied to the Control of *Bordetella bronchiseptica* Rhinitis in Swine," Iowa State University, Ames, Iowa, Dr. William P. Switzer, Major Professor. This thesis is on deposit at the Iowa State University Library, Ames, Iowa under call No. 1974-F 249. This thesis also contains a description of the taxonomic characteristics of strain 55.

Strain 55 was isolated in 1955 by Dr. William P. Switzer from the pneumonic lungs and normal nasal cavity of an experimental pig inoculated intranasally with crude pneumonic swine lung suspension. The initial inoculum was secured from a pig in a herd experiencing clinical atrophic rhinitis and pneumonia. This organism was seeded into rubber stoppered 100 milliliter vials of tryptose phosphate broth (TPB) in 1955 and incubated at 37° C. These vials were then committed to a duration of survival trial. The cultures were sampled several times during the ensuing years and found to be viable. In January of 1972, after 17 years without serial passage, contents of a vial were cultured by Daniel O. Farrington on 5% horse blood agar. Two extremely rough bacterial colonies developed and 1 colony was picked into TPB. This organism was subsequently identified as a highly modified *B. bronchiseptica* and designated as Strain 55.

Tests conducted by Daniel O. Farrington, as part of his Ph.D. thesis work identified above, compared strain 55 with a virulent strain of *B. bronchiseptica* (strain B) and with an attenuated strain (strain D-1). Several differences were found. These were: (1) Strain 55 colonies on modified McConkey's agar medium without Furaltadone incubated at 37° C. had a "lacy" margin. Strains D-1 and B colony margins were undulate. The colony diameter at 48 hours was approximately 1 ml. with colonies up to several millimeters in diameter present after prolonged incubation. All 3 strains formed colonies on 5 percent horse blood agar that were circular, smooth, opaque, and homogenous with an entire edge. The colony size and morphology of the *B. bronchiseptica* strain varied greatly depending on the concentration of organism on the culture plate, hours (days) of incubation at 37° C. or room temperature and the relative humidity under which the culture plates were maintained. Aged colonies on modified MacConkey's agar without Furaltadone were characterized by central collapse of the colony and pronounced undulating rays from the cell margin giving the colony a "wagon wheel" shape. (2) Strains D-1 and B were motile while 55 strain was often nonmotile when examined by the hanging drop method. (3) Strain 55 was sensitive to Furaltadone at the 0.02 mg./ml. concentration in the modified MacConkey's medium while D-1 and B strain were not. (4) Strain 55 gave a slow and weak positive reaction (<24 hours) on Simmon's citrate gear slants while D-1 and B strains were strongly positive at 18 to 24 hours. (5) Strain 55 had the highest hemagglutinating titer among the 3 strains.

Subsequently, there has been further characterization of strain 55. It has been found that this strain has two plasmids, one of 31 megadaltons and one of 3 megadaltons. In addition, the d2 cell membrane protein is greater in amount than other strains, such as strain B (virulent) and strain D-1 (avirulent).

When viable cells of strain 55 are deposited in sufficient numbers in the nasal passages of swine, they multiply and form colonies in the mucous membranes of the nasal passages. The colonies persist for only a few days, and are usually cleared from the nasal passages of swine in less than a week. When the strain 55 cells are applied to the nasal or other respiratory mucosa of dogs, colonies at first form and are then cleared. With dogs the colonies persist for a somewhat longer time, several weeks being required for clearance. During the time in which the colonies of strain 55 are present in the respiratory mucosa of the animals, they do not produce any clinical symptoms of disease. However, when used as an intrarespiratory vaccine for non-immune animals subject to *Bordetella bronchiseptica* infection, the resistance of the animals to subsequent infection by virulent *B. bronchiseptica* is significantly increased. The local immunization inhibits the growth of infectious *B. bronchiseptica,* and greatly accelerates the clearance rate. In swine, clinical symptons of atrophic rhinitis are prevented, and the subsequent atrophy of the turbinate is greatly reduced. In dogs, clinical symptoms of kennel cough (tracheobronchitis) are prevented.

In preparing the vaccine of the present invention, viable cells of *Bordetella bronchiseptica* strain ATCC No. 31427, which may have been subjected to freeze-drying for preservation, are introduced into a suitable culture medium, which is then incubated at a temperature favoring the growth of the organism. In general, published procedures for culturing *B. bronchiseptica* organisms are employed. See, for example, *Am. J. Vet. Res.,* 30, 1161, 1162 (1969); and *Am. J. Vet. Res.,* 33, 975, at 1976 (1972). More specifically, tryptose phosphate broth (TPB) may be used for propagation of the organism. One suitable source of such a TPB medium is Difco Laboratories, Inc., Detroit, Mich. Other useable culture mediums include: Bordet-Gengou Agar (Difco), Brain-Heart Infusion Broth (Difco), tryptone soya broth (Oxoid Limited, London, England). Propagation temperatures of 36° to 38° are favorable.

The cultured cells are preferably recovered (harvested) without concentration by centrifugation or filtration. Since the cells are to be used live, it is desirable to avoid damage to the cells by mechanical processing. Cell cultures having sufficiently high concentration of the strain 55 cells for direct use as a vaccine are readily obtainable. The residual culture nutrients and growth by-products can remain with the cells for vaccine administration.

For vaccine use, strain 55 cells are preferably employed as an aqueous suspension, which can be readily administered to the animals by application to the nasal mucosa. For example, the aqueous suspension of the cells may be introduced into the nasal passages in a measured amount by means of a syringe, or a measured amount of the aqueous cell suspension may be sprayed into the nostrils. The cell suspension should therefore be sufficiently liquid so that it is readily administerable or sprayable. Depending on the animals with which the vaccine is to be used and the amount of the cell suspension to be intranasally administered, the concentration of viable cells may vary over a wide range. For example, concentrations of from $10^3$ to $10^8$ can be used. Even with small animals such as guinea pigs and rabbits, however, it will usually be desirable to administer at least one thousand viable cells per nostril, making a total dose of $2 \times 10^3$ cells. Larger doses for swine and dogs are desirable, such as at least $1 \times 10^5$ viable cells per milliliter. Usually, the optimum dose will be within the range from $1 \times 10^5$ to $1 \times 10^7$ cells per millimeter.

While a degree of immunization may be obtained by introducing the vaccine into one nostril of the animal or elsewhere in the respiratory tract, the preferred procedure for swine is to introduce approximately equal amounts of the aqueous cell suspension into both nostrils (nares). The dose volume tends to be limited by the amount of liquid that the nostrils can retain. For example, the total dose (both nostrils) may range from about 0.5 to 1.5 ml. of the suspension. As indicated, this dose may be divided approximately equally between the two nostrils. For example, from about 0.3 to 0.7 ml. of the suspension may be introduced into each nostril. A convenient dose size is 0.5 ml. per nostril.

For administration to swine, the preferred procedure is intranasal vaccination, as described above. This procedure can also be used for dogs. However, it is now believed that the best mode of administration to dogs it to apply the vaccine to the mucosa of the pharynx.

For the purposes of the present invention, cell counts may be made by standard procedures. The cell concentrations per milliliter of the vaccine are determined by plating the cells and counting the CFU (colony forming units). The propagation for determining CFU may be on standard plates, such as 5% horse blood agar, T.P.B. agar on McConkey's agar.

The vaccines of this invention and the results which can be obtained by their use are further illustrated by the following experimental examples.

EXAMPLE 1

Three milliliters of sixth passage strain 55 modified *B. bronchiseptica* 24-hour tryptose phosphate broth (TPB) culture was inoculated into cotton-stoppered flasks containing 50 ml. of TPB and incubated at 37° C. for 24 or 48 hours. The live seventh passage TPB cultures of strain 55 were used for intranasal vaccination of swine. Twenty-four hour cultures were administered for the first dose and forty-eight hour cultures were used for the second and subsequent doses. The 24-hour strain 55 seventh passage TPB culture contained approximately $1 \times 10^6$ organisms/ml. and the 48-hour TPB culture approximately $1 \times 10^7$ organisms/ml. These titers were determined as colony forming units (CFU) on 5% horse blood agar. The vaccines were administered on the day of their preparation.

A dosage of 0.5 ml. per nostril of the 24 and 48 hour TPB cultures in the form of nosedrops was administered to each intranasally immunized pig. The tip of a 5 milliliter syringe was inserted into each nostril and used to instill the TPB culture into the nasal cavity. Administration of the culture was timed with the inspiration of the pig.

The ability of live, low-virulence strain 55 *B. bronchiseptica* intranasal vaccination to produce nasal resistance to subsequent challenge with a swine-virulent *B. bronchiseptica* (strain B) was tested. The nasal persistence of strain 55 infection was also evaluated.

Thirteen pigs, 4-to-8-weeks of age, were obtained from rhinitis free herds. All pigs were culture-negative for *B. bronchiseptica*. The pigs were selected into two groups and housed in individual isolation units.

Six pigs received 3 doses over a 4 day period of live, low-virulence strain 55 intranasal vaccine at 7 weeks of age and seven pigs served as nonvaccinated controls. All pigs were challenged with virulent *B. bronchiseptica* (strain B) 3 weeks post-intranasal vaccination. Strain 55 was not detected by the nasal swab culture method in the nasal secretions of the vaccinated pigs 2 weeks post-intranasal vaccination.

A summary of the incidence of *B. bronchiseptica* in the nasal secretions of the B strain challenged pigs is presented in Table A. At 3 weeks post-B strain challenge 0 of 6 vaccinates and 5 of 7 control pigs were culture-positive for *B. bronchiseptica*. At 4 weeks post-B strain challenge the nasal secretions of 3 of 6 vaccinated pigs were culture-positive for *B. bronchiseptica* with an average colony count of 6 organisms per culture plate. The 8 week termination figures were 0 of 6 and 7 of 7 respectively. The average termination PAST serum titer was 39 for the vaccinated pigs and 53 for the nonvaccinated controls. At necropsy, gross examination revealed all intranasally immunized pigs had normal nasal turbinates while 2 of 3 controls examined had moderate to severe turbinate atrophy.

The procedure for the determination of gross turbinate atrophy was as follows: A cross-section of the nasal cavity was made at the level of the second premolar tooth. Gross distortion or atrophy of the nasal turbinates and nasal septal defects were characterized depending on severity as mild, moderate or severe.

TABLE A

| Swine/Product | Number of Swine | Number of swine culture-positive for *B. bronchiseptica* over number sampled | | | | | Gross evidence of Turbinate Atrophy at necropsy |
|---|---|---|---|---|---|---|---|
| | | Pretrial | Weeks after virulent B strain *B. bronchiseptica* challenge | | | | |
| | | | 3 | 4 | 6 | 8 | |
| 4 to 8-week old pigs live low-virulence strain 55 intranasal vaccination | 6 | 0/6 | 0/6 | 3/6 | 0/6 | 0/6 | 0/6[a] |
| 4 to 8-week old pigs non-vaccinated | 7 | 0/7 | 5/7 | 6/7 | 6/7 | 7/7 | 2/3 |

TABLE A-continued

| Swine/Product | Number of Swine | Number of swine culture-positive for B. bronchiseptica over number sampled | | | | | Gross evidence of Turbinate Atrophy at necropsy |
| --- | --- | --- | --- | --- | --- | --- | --- |
| | | Pretrial | Weeks after virulent B strain B. bronchiseptica challenge | | | | |
| | | | 3 | 4 | 6 | 8 | |
| controls | | | | | | | |

[a]Number of pigs showing gross turbinate atrophy over number necropsied.

EXAMPLE 2

The ability of live, low-virulence strain 55 *B. bronchiseptica* intranasal vaccination to produce nasal resistance to subsequent challenge with B strain swine-virulent *B. bronchiseptica* was reevaluated. The nasal persistance of strain 55 was also evaluated.

Ten pigs, 3-to-4-weeks of age, were obtained from a Bordetella rhinitis-free herd. The pigs were randomly selected into 3 groups and placed in individual isolation units.

Six pigs received 3 doses over a 4 day period of live, low-virulence strain 55 *B. bronchiseptica* intranasal vaccine, and 4 pigs served as unvaccinated controls. All pigs were challenged with swine-virulent strain B 2 weeks post-intranasal immunization. The strain 55 *B. bronchiseptica* was not detected on nasal swab culture 6 days post-vaccination. The pigs were 4 to 5 weeks of age at the time of strain 55 vaccination and 6 to 7 weeks of age at the time of B strain challenge.

A summary of the incidence of *B. bronchiseptica* in the nasal secretions of the B strain challenged pigs during the first 12 weeks of the experiment is presented in Table B. At 2 weeks post-B strain challenge 0 of 4 live, 55 strain vaccinates, and 4 of 4 control pigs were culture-positive for *B. bronchiseptica*. The 12 week figures were 0 of 5, and 1 of 4.

At 8 weeks and 17 weeks post-first B strain challenge, the live strain 55 intranasally vaccinated pigs were re-challenged with B strain. *Bordetella bronchiseptica* was not detected in the nasal secretions of live, low-virulence strain 55 intranasally vaccinated pigs for the entire 19 week sampling period.

The average termination PAST serum titer was 38 for the live 55 strain vaccinates, and 13 for the nonvaccinated controls. At necropsy, gross examination revealed all intranasally vaccinated pigs had normal turbinate structures while 3 of 4 controls had mild turbinate atrophy.

EXAMPLE 3

There is no evidence to indicate the persistance in or transfer between swine of strain 55 *B. bronchiseptica*. In the absence of demonstrable swine to swine transfer for the determination of potential increased virulence of strain 55, the organism was back passaged through 11 passages in 6-to-8-day old embryonating hens eggs and introduced into the nasal cavities of susceptible 3-week-old pigs. Strain 55 *B. bronchiseptica* killed 100 percent of the embryos by 72 hours in the first passage. Swine virulent B strain *B. bronchiseptica* regularly kills 100 percent of 6-to-8-day-old chicken embryos by 24 hours post-yolk sac inoculation. An increase in the virulence (earlier mortality) of 55 strain for chicken embryos was not evidenced through 11 serial passages. Strain 55 eleventh passage egg yolk inoculum was not detected in the nasal secretions of the intranasally inoculated pigs at 1 or 2 weeks post-inoculation.

EXAMPLE 4

Ten mixed bred eight week old dogs were placed in canine testing facilities and fed a commercial dry dog ration. The dogs were held until determined to be negative for *Bordetella bronchiseptica* by nasal swab culturing. The ten dogs were randomly divided into two groups of 5 dogs each. Group I designated control dogs were maintained in a separate facility while the Group II treated dogs were immunized. Each of the 5 dogs of Group II were exposed to an aerosol formed from an aqueous suspension of viable strain 55 *B. bronchiseptica,* thereby exposing the respiratory mucosa of the dogs to the strain 55 cells. The estimated dose was $2.5\times10^9$ cells per dog. Each treated dog was swabbed daily for 14 days to determine the longevity of the strain 55 on the dog's respiratory mucosa. Swabbing was conducted periodically 79 days post-challenge. Each dog was also observed for any clinical signs of kennel cough e.g. productive coughing or coughing on palpation.

On day 14 post-exposure to strain 55 each dog of Groups I and II was challenged with a virulent *Bor-*

TABLE B

| Swine/Product | Number of Swine | Number of swine positive for *B. bronchiseptica* over number sampled: Pretrial | Weeks after virulent B strain *B. bronchiseptica* challenge: 2 | 4 | 6 | 8 | 12 | Gross Evidence of Turbinate Atrophy at Necropsy |
|---|---|---|---|---|---|---|---|---|
| 5-week old pigs live, low-virulence strain 55 intranasal vaccination | 5 | 0/5 | 0/4[a] | 0/5 | 0/5 | 0/5 | 0/5 | 0/4[b] |
| 4 to 5-week old pigs non-vaccinated controls | 4 | 0/4 | 4/4 | 3/4 | 3/4 | 2/4 | 1/4 | 3/4 |

[a]One sample was not interpretable due to overgrowth with contaminating organisms.
[b]Number of pigs with turbinate atrophy at necropsy over number of pigs examined.

*detella bronchiseptica* strain. Cultures of the *Bordetella bronchiseptica* virulent strain were grown 24 hours in brain-heart infusion media at 37° C. The cultures were propagated in stationary culture. The challenge culture contained approximately $2.0 \times 10^8$ cells/ml. Each test dog's nose was placed in a one cubic foot plastic box and exposed to air saturated with the virulent *Bordetella bronchiseptica* for 2.5 minutes. All ten dogs were then housed in the same pen.

The daily swab samples referred to above were taken from each naris of each test dog. The two swabs were added to a tube containing 1 ml sterile normal saline. 0.1 ml amounts of the resulting solution was plated on modified MacConkey's Agar containing 1% dextrose and 50 units/ml mycostatin. The plates were incubated 72 hours at 37° C. to allow colony formation of both the slow growing strain 55 and more rapid growing challenge strain. Both strain 55 and the challenge strain organism were quantitated.

During the test, each dog was observed daily for clinical signs of kennel cough. Each dog was also nasal swabbed twice weekly for 79 days post-challenge. The results were as follows:

1. All test dogs were negative for *Bordetella bronchiseptica* at test initiation.
2. Five of five treated dogs were positive for strain 55 on each of fourteen days post-exposure.
3. One of five intranasally treated-challenged dogs demonstrated clinical signs of kennel cough for four days continually while five of five non-treated-challenged demonstrated severe clinical kennel cough for 11–16 days post-challenge. The one dog which did demonstrate clinical signs of kennel cough also demonstrated a significantly lower level of immunizing strain 55 and a significantly higher level of the virulent challenge strain that was found on the average in the treated-challenged dogs which demonstrated no clinical signs of kennel cough.
4. There was a highly significant suppression of virulent *Bordetella bronchiseptica* strain organisms in the strain 55 treated dogs as compared to the untreated challenged dogs, as shown by Table C.

TABLE C

| Days Post Challenge | Average No. Challenge Organisms/Dog (CFU's) | | |
|---|---|---|---|
| | Vaccinates | Controls | % Difference |
| 6 | $3.9 \times 10^2$ | $2.1 \times 10^5$ | 99.9 |
| 19 | $9.6 \times 10^2$ | $9.0 \times 10^5$ | 99.9 |
| 29 | $1.1 \times 10^3$ | $3.6 \times 10^5$ | 99.9 |
| 40 | $1.3 \times 10^2$ | $4.2 \times 10^4$ | 99.9 |

In the test of the foregoing example, the strain 55 cells are found to be present in the nasal mucosal tissue of each of the five inoculated dogs for up to 40 days post-immunization. In general, strain 55 cells persist for a longer time in the nasal passages of dogs than they do in swine. For example, strain 55 cells may maintain colonization in large numbers on the intranasal mucosa for 7 to 20 days post-installation, with the clearance of the cells being obtained by about 50 to 75 days after inoculation.

We claim:

1. An intra-respiratory vaccine for animals subject to *Bordetella bronchiseptica* infection, comprising an aqueous suspension of viable cells of the modified *Bordetella bronchiseptica* identified as ATCC strain No. 31437, said strain being capable of propagation at 37° C. in a suitable culture medium, said aqueous suspension containing at least $2 \times 10^3$ of said viable cells per milliliter.

2. The vaccine of claim 1 in which said aqueous suspension contains at least $1 \times 10^5$ of said viable cells per milliliter.

3. An intra-respiratory vaccine for animals subject to *Bordetella bronchiseptica* infection, comprising a sprayable suspension of viable cells of the modified *Bordetella bronchiseptica* identified as ATCC strain No. 31437, said strain being capable of propagation at 37° C. in a suitable culture medium, said aqueous suspension containing from $1 \times 10^5$ to $1 \times 10^7$ of said viable cells per milliliter, and also containing residual culture nutrients.

4. An intranasal vaccine for swine, comprising an intranasally-administrable aqueous suspension of viable cells of the modified *Bordetella bronchiseptica* identified as ATCC strain No. 31437, said strain being capable of propagation at 37° C. in a suitable culture medium, said aqueous suspension containing from $1 \times 10^5$ to $1 \times 10^7$ per milliliter of said viable cells and also containing residual culture nutrients.

5. The method of increasing the resistance of animals to *Bordetella bronchiseptica* infection which animals are otherwise subject to said infection, comprising applying to the respiratory mucosa of said animals a resistance-increasing effective amount of viable cells of the modified *Bordetella bronchiseptica* identified as ATCC strain No. 31437, said strain being capable of propagation at 37° C. in a suitable culture medium.

6. The method of claim 5 in which said animals are swine.

7. The method of claim 5 in which said animals are dogs.

8. The method of increasing the resistance of swine to *Bordetella bronchiseptica* infection, comprising introducing into the nostrils of the swine an aqueous suspension containing at least $1 \times 10^5$ viable cells per milliliter of the modified *Bordetella bronchiseptica* identified as ATCC strain No. 31437, said strain being capable of propagation at 37° C. in a suitable culture medium, from 0.5 to 1.5 milliliters of said suspension being administered per animal.

9. The method of claim 8 in which approximately equal amounts of said cell suspension are introduced into each nostril of the swine, the amount per nostril being from 0.3 to 0.7 milliliters of a suspension which contains from $1 \times 10^5$ to $1 \times 10^7$ per milliliter of said viable cells.

10. The method of increasing the resistance of an animal to *Bordetella bronchiseptica* infection, said animal being selected from the class consisting of swine and dogs, comprising applying to the respiratory mucosa of the animal at least $1 \times 10^5$ viable cells per animal of the modified *Bordetella bronchiseptica* identified as ATCC strain No. 31437, said strain being capable of propagation at 37° C. in a suitable culture medium.

11. The method of claim 10 in which said cells are introduced in the form of an aqueous suspension, and approximately equal amounts of said suspension are introduced into each nostril of the animal.

12. The method of claim 11 in which the amount of said suspension introduced per nostril is from about 0.3 to 0.7 milliliters of a suspension which contains from $1 \times 10^5$ to $1 \times 10^7$ per milliliter of said viable cells.

* * * * *